United States Patent
Hetrick

(10) Patent No.: US 9,974,733 B1
(45) Date of Patent: May 22, 2018

(54) TANNING MASSAGE CREME, EXTENDER, BUFFER AND METHOD OF APPLICATION

(71) Applicant: Tamela Sue Hetrick, Lewistown, PA (US)

(72) Inventor: Tamela Sue Hetrick, Lewistown, PA (US)

(*) Notice: Subject to any disclaimer, the term of this patent is extended or adjusted under 35 U.S.C. 154(b) by 299 days.

(21) Appl. No.: 14/675,784

(22) Filed: Apr. 1, 2015

Related U.S. Application Data

(60) Provisional application No. 61/974,103, filed on Apr. 2, 2014.

(51) Int. Cl.
| | |
|---|---|
| *A61K 36/00* | (2006.01) |
| *A61K 8/97* | (2017.01) |
| *A61K 8/92* | (2006.01) |
| *A61K 8/67* | (2006.01) |
| *A61K 8/35* | (2006.01) |
| *A61K 8/60* | (2006.01) |
| *A61Q 19/04* | (2006.01) |

(52) U.S. Cl.
CPC .................. *A61K 8/97* (2013.01); *A61K 8/35* (2013.01); *A61K 8/60* (2013.01); *A61K 8/678* (2013.01); *A61K 8/92* (2013.01); *A61Q 19/04* (2013.01); *A61K 2800/28* (2013.01)

(58) Field of Classification Search
CPC ...................................................... A61K 36/00
See application file for complete search history.

(56) References Cited

U.S. PATENT DOCUMENTS

2008/0292734 A1* 11/2008 Hill .......................... A61K 8/97
424/738

* cited by examiner

*Primary Examiner* — Qiuwen Mi
(74) *Attorney, Agent, or Firm* — John J. Elnitski, Jr.

(57) ABSTRACT

The present invention is a massage tanning crème formula to color skin of a person to appear tanned. The application of the formula, first including performing an exfoliation of areas to be colored. Then, including the application of a massage tanning crème formula in an even coat to ensure an even tan color, where the tanning cream is a mixture of Organic Aloe Vera (Barbadensis Miller) Juice; Emulsifying Wax; Organic Virgin Coconut (*Cocos Nucifera*) Oil; Virgin Cocoa Butter (*Theobroma Cacao*); Sunflower Oil (*Helianthus Annuus*); Hydrolyzed Oats; Vitamin E; Wasabi (*Wasabia Japocica*) Root Extract; Ginger (*Zingiber Officinali*) Root Extract; Garlic (*Allium Sativum*) Bulb Extract; Dihydroxyacetone; and Eurythulose.

10 Claims, No Drawings

TANNING MASSAGE CREME, EXTENDER, BUFFER AND METHOD OF APPLICATION

This application claims the benefit of and incorporates by reference U.S. Provisional Application No. 61/974,103, filed Apr. 2, 2014

BACKGROUND

The present invention generally relates to massage crèmes and method of application of massage crèmes. More specifically, the present invention relates to massage crèmes and application of massage cream which color human skin to reproduce an appearance of being sun tanned.

There are many massage and tanning lotions on the market. Tanning lotions tend to streak, when applied by the user. Many tanning lotion produce a color that does not realistically appear as if a person was out in the sun and their skin tanned due to exposure to the sun. Massage crèmes do not produce a tanned effect on a person's skin. What is needed is a massage crème and method of application which produces a realistic appearance as if a person was out in the sun and their skin tanned due to exposure to the sun, without streaking or dying of the skin.

It is an object of the present invention to provide a massage crème and method of application which produces a realistic appearance as if a person was out in the sun and their skin tanned due to exposure to the sun.

SUMMARY OF THE INVENTION

The present invention is a massage tanning crème formula to color skin of a person to appear tanned. The application of the formula, first including performing an exfoliation of areas to be colored. Then, including the application of a massage tanning crème formula in an even coat to ensure an even tan color, where the tanning cream is a mixture of Organic Aloe Vera (Barbadensis Miller) Juice; Emulsifying Wax; Organic Virgin Coconut (*Cocos Nucifera*) Oil; Virgin Cocoa Butter (*Theobroma Cacao*); Sunflower Oil (*Helianthus Annuus*); Hydrolyzed Oats; Vitamin E; Wasabi (*Wasabia Japocica*) Root Extract; Ginger (*Zingiber Officinali*) Root Extract; Garlic (*Allium Sativum*) Bulb Extract; Dihydroxyacetone; and Eurythulose.

DETAILED DESCRIPTION

The present invention is a tanning massage crème, extender, buffer and method of application. The tanning massage crème according to the present invention, unlike tanning lotions on the market today, is formulated to absorb slowly into skin. This enables a massage therapist to ensure that an even coat is applied to a person and when dry will not streak. The person may use a tanning extender according to present invention, which they rub into their skin to extend the tanned appearance.

The optimal formula for the tanning massage crème according to the present invention includes following ingredients: 60.7% Organic Aloe Vera (Barbadensis Miller) Juice 7.69% Emulsifying Wax; 10.82% Organic Virgin Coconut (*Cocos Nucifera*) Oil; 7.74% Virgin Cocoa Butter (*Theobroma Cacao*); 2.5% Sunflower Oil (*Helianthus Annuus*); 1% Hydrolyzed Oats; 0.40% Vitamin E; 0.05% Wasabi (*Wasabia Japocica*) Root Extract; 0.05% Ginger (*Zingiber Officinali*) Root Extract; 0.05% Garlic (*Allium Sativum*) Bulb Extract; 6% Dihydroxyacetone; 3% Eurythulose.

The optimal formula for the tanning extender massage crème according to the present invention includes following ingredients: 66.7% Organic Aloe Vera (Barbadensis Miller) Juice; 7.69% Emulsifying Wax; 10.07% Organic Virgin Coconut (*Cocos Nucifera*) Oil; 6.99% Virgin Cocoa Butter (*Theobroma Cacao*); 2.5% Sunflower Oil (*Helianthus Annuus*); 1% Hydrolyzed Oats; 0.40% Vitamin E; 0.05% Wasabi (*Wasabia Japocica*) Root Extract; 0.05% Ginger (*Zingiber Officinali*) Root Extract; 0.05% Garlic (*Allium Sativum*) Bulb Extract; 3% Dihydroxyacetone; 1.5% Eurythulose.

The optimal formula for the buffer according to the present invention includes following ingredients: 22.22% Organic Virgin Cocoa Butter (*Theobroma Cacao*); 22.22% Shea Butter (*Butyrospermum Parkii*); 22.22% Organic Virgin Coconut (*Cocos Nucifera*) Oil; 33.34% Sunflower Oil (*Helianthus Annuus*).

Any of the ingredients contained in each of the above formulas for the tanning crème, extender or buffer may be increased or decreased by five percent of the above stated percentages. A massage crème in general is a mixture of oil, liquid and an emulsifier. The oil phase of the crème is a non dissolving oil. The liquid phase of the crème is a dissolving liquid such as water, juice, wine, beer, etc. The emulsifier holds the oil and liquid molecules together and without the emulsifier the oil floats on the liquid. The Aloe Vera juice of the tanning massage crème and the tanning extender crème formulas is the liquid phase. The Aloe Vera juice can be substituted for by other dissolving liquids such as water. The Aloe Vera juice was chosen to provide therapeutic benefits that water does not provide in its self. The Emulsifying Wax of the tanning massage crème and the tanning extender crème formulas is the emulsifier. It is envisioned that both the Aloe Vera juice and Emulsifying Wax can be replaced with comparable replacements to create a crème, but these components being replaced will not be optimal.

The method of application of the tanning massage crème begins with a full body exfoliation of the person to ensure that the tan effect lasts for approximately 10 to 14 days. This is done with an exfoliating mitt that is worn by the Therapist. The exfoliating mitt is made from 100% agave fibers. The person's skin is brushed with the mitt in the direction of blood flow. Exfoliating mitts are known and have an abrasive surface that is safe for use on skin. The exfoliation process removes dead skin cells so the person's skin can breathe. Exfoliation also warms the skin by increasing circulation and opens pores allowing the tanning massage crème to be absorb deep into skin. Certain high keratin areas of a person's body (around nails, elbows, knees) will absorb more tanning crème. After the exfoliation process, the high keratin areas of the body are be treated by using the buffer formula described above to keep those areas from absorbing too much of the tanning massage crème. The blend of butters and oils of the buffer are applied by the therapist and left to rest for five minutes on the body, in order to be absorbed by the body before the next step.

The tanning massage crème is then applied to the person. The therapist will wear gloves to protect their hands from discoloring. The therapist will apply the tanning crème formula described above in an even coat to ensure an even tan and massage the crème on and into the body so that it is absorbed into the skin. The person will then rest for ten minutes to ensure the tanning crème formula has fully absorbed into the skin. The formulas of the tanning massage crème, buffer and extender do not dye or stain the users skin. The tanning massage crème formula is white and changes in color, which will not be seen for a few hours. This is because tanning massage crème formula is 100% natural ingredients and when applied to the skin reacts with the amino acids already present in the skin. This reaction to cause a tanning color of the skin will continue to develop for up to 48 hours after application of the tanning massage crème formula.

The person to whom the tanning massage crème formula has been applied, should avoid any activity for four hours that produces perspiration or requires skin to be in water, including pedicures and manicures. The tanning massage crème formula, unlike tanning lotions on the market today, is formulated to absorb slowly into skin. This enables the massage therapist to ensure that an even coat is applied, so when dry, there will be no streaking. The extender formula is used to extend the length of time the skin remains a tanned color. The person uses the extender formula by rubbing the extender formula into their skin to extend the tanned look.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention that is to be given the full breadth of any and all equivalents thereof.

I claim:

1. A tanning massage cream comprising an effective amount of: Organic Aloe Vera Juice; Emulsifying Wax; Organic Virgin Coconut Oil; Virgin Cocoa Butter; Sunflower Oil; Hydrolyzed Oats; Vitamin E; Wasabi Root Extract; Ginger Root Extract; Garlic Bulb Extract; and Dihydroxyacetone; Erythrulose.

2. The tanning massage cream of claim 1, wherein there is 60.7% Organic Aloe Vera Juice; 7.69% Emulsifying Wax; 10.82% Organic Virgin Coconut; 7.74% Virgin Cocoa Butter; 2.5% Sunflower Oil; 1% Hydrolyzed Oats; 0.40% Vitamin E; 0.05% Wasabi Root Extract; 0.05% Ginger Root Extract; 0.05% Garlic Bulb Extract; 6% Dihydroxyacetone; and 3% Erythrulose.

3. The tanning massage cream of claim 1, wherein there is 66.7% Organic Aloe Vera Juice; 7.69% Emulsifying Wax; 10.07% Organic Virgin Coconut Oil; 6.99% Virgin Cocoa Butter; 2.5% Sunflower Oil; 1% Hydrolyzed Oats; 0.40% Vitamin E; 0.05% Wasabi Root Extract; 0.05% Ginger Root Extract; 0.05% Garlic Bulb Extract; 3% Dihydroxyacetone; and 1.5% Erythrulose.

4. The tanning massage cream of claim 2, wherein said percentage of any one ingredient of said tanning massage cream is adjusted by 0.0 to 5.0% of said percentage.

5. The tanning massage cream of claim 3, wherein said percentage of any one ingredient of said tanning massage cream is adjusted by 0.0 to 5.0% of said percentage.

6. A tanning massage cream comprising an effective amount of: Aloe Barbadensis Miller; Emulsifying Wax; *Cocos Nucifera; Theobroma Cacao; Helianthus Annuus*; Hydrolyzed Oats; Vitamin E; *Wasabia Japonica; Zingiber Officinali; Allium Sativum* Bulb Extract; Dihydroxyacetone; Erythrulose.

7. The tanning massage cream of claim 6, wherein there is 60.7% Organic Aloe Barbadensis Miller; 7.69% Emulsifying Wax; 10.82% *Cocos Nucifera;* 7.74% *Theobroma Cacao;* 2.5% *Helianthus Annuus;* 1% Hydrolyzed Oats; 0.40% Vitamin E; 0.05% *Wasabia Japonica* Root Extract; 0.05% *Zingiber Officinali;* 0.05% *Allium Sativum;* 6% Dihydroxyacetone; 3% Erythrulose.

8. The tanning massage cream of claim 6, wherein there is 66.7% Aloe Barbadensis Miller; 7.69% Emulsifying Wax; 10.07% *Cocos Nucifera;* 6.99% *Theobroma Cacao;* 2.5% *Helianthus Annuus;* 1% Hydrolyzed Oats; 0.40% Vitamin E; 0.05% *Wasabia Japonica;* 0.05% *Zingiber Officinali;* 0.05% *Allium Sativum;* 3% Dihydroxyacetone; 1.5% Erythrulose.

9. The tanning massage cream of claim 7, wherein said percentage of any one ingredient of said tanning massage cream is adjusted by 0.0 to 5.0% of said percentage.

10. The tanning massage cream of claim 8, wherein said percentage of any one ingredient of said tanning massage cream is adjusted by 0.0 to 5.0% of said percentage.

* * * * *